United States Patent [19]

Sköld

[11] Patent Number: 5,447,723
[45] Date of Patent: Sep. 5, 1995

[54] USE OF A TRIETHANOLAMINE PRODUCT MIXTURE

[75] Inventor: Rolf Sköld, Stenungsund, Sweden

[73] Assignee: Berol Nobel AB, Stenungsund, Sweden

[21] Appl. No.: 211,218

[22] PCT Filed: Oct. 7, 1992

[86] PCT No.: PCT/SE92/00700

§ 371 Date: Mar. 24, 1994

§ 102(e) Date: Mar. 24, 1994

[87] PCT Pub. No.: WO93/06814

PCT Pub. Date: Apr. 15, 1993

[30] Foreign Application Priority Data

Oct. 10, 1991 [SE] Sweden ................ 9102931

[51] Int. Cl.$^6$ .................................................. A61K 7/50
[52] U.S. Cl. .................... 424/401; 424/70.1; 514/844; 514/845; 514/846; 514/848
[58] Field of Search ............... 424/70.1, 401; 514/844, 514/845, 846, 848

[56] References Cited

U.S. PATENT DOCUMENTS

| | | | |
|---|---|---|---|
| 4,070,309 | 1/1978 | Jacobsen | 252/547 |
| 4,235,898 | 11/1980 | Watanabe et al. | 424/245 |
| 4,273,937 | 6/1981 | Gum et al. | 564/2 |
| 4,725,319 | 2/1988 | Osberghaus | 134/4 |
| 4,820,308 | 4/1989 | Madrange et al. | 8/405 |

FOREIGN PATENT DOCUMENTS

0286075A2 10/1988 European Pat. Off. .
0344564A1 12/1989 European Pat. Off. .
0379093A1  7/1990 European Pat. Off. .

*Primary Examiner*—Gollamundi S. Kishore
*Assistant Examiner*—Sharon Howard
*Attorney, Agent, or Firm*—Spencer, Frank & Schneider

[57] ABSTRACT

A method of providing a cosmetic product or a cleaning composition with defoaming properties, includes adding to the cosmetic product or the cleaning composition a triethanolamine product mixture which has not been distilled and which is composed of a major part by weight of triethanolamine; a minor part by weight of diethanolmono-$C_{3-4}$-alkanolamine and monoethanoldi-$C_{3-4}$-alkanolamine; and less than 1% by weight of a mixture of diethanolamine and monoethanolamine. Preferably, the triethanolamine product mixture is composed of from 60–90% by weight of triethanolamine; from 10–40% by weight of a mixture of diethanolmono-$C_{3-4}$-alkanolamine and monoethanoldi-$C_{3-4}$-alkanolamine; and less than 1% by weight of a mixture of diethanolamine and monoethanolamine.

4 Claims, No Drawings

USE OF A TRIETHANOLAMINE PRODUCT MIXTURE

BACKGROUND OF THE INVENTION

1. Field of the Invention

The present application relates to the use of a triethanolamine product mixture having a low content of diethanolamine and monoethanolamine in cosmetic products, such as shampoos and creams, and cleaning compositions, e.g., for hard surfaces.

2. Description of the Related Art

The use of triethanolamine in a variety of cosmetic products, and cleaning compositions is well known. Triethanolamines are normally produced in one or more steps by ethoxylating ammonia with ethylene oxide. In order to avoid the formation of polyalkyleneglycol chains, $HOC_2H_4(OC_2H_4)_n$, where $n>0$, and the quaternization of the nitrogen atom, the ethoxylation is normally stopped when the reaction mixture contains 60-90% by weight of triethanolamine and 10-40% by weight of diethanolamine and monethanolamine. Such a reaction mixture may be subjected to distillation to obtain purer triethanolamine. The fact that the triethanolamine reaction product contains a large amount of diethanolamine has not previously been considered a real drawback, as diethanolamine contributes to anticorrosion properties when used in functional fluids and to a desired alkalinity and foam stabilization when used in cosmetic products and cleaning compositions.

Recently, more attention has been paid to the fact the diethanolamine is toxic and forms nitrosamines, which are carcinogenic in animal tests. Therefore, a reduction of the content of diethanolamine is desirable. The content should according to recommentations be less than 1% by weight.

Thus, one object of the invention is to produce a triethanolamine product mixture which contains diethanolamine in an amount less than 1% by weight. This triethanolamine product mixture shall at least have about the same foam stabilizing properties in cosmetics and cleaning products as triethanolamine.

Another object of the invention is that the method of producing a triethanolamine product mixture shall be simple to perform and that the mixture shall be usable without any additional cleaning and/or working-up processes, such as distillation.

Still another object of the invention is to keep the formation of quarternized triethanolamine and polyalkylene glycol chain containing ethanolamine products to a low level.

SUMMARY OF THE INVENTION

According to the invention it has now been found that these objects can be met by using in cosmetic products, and cleaning compositions, a triethanolamine mixture containing a major part of triethanolamine, a minor part of diethanolmono-$C_{3-4}$-alkanolamine and monoethanoldi-$C_{3-4}$-alkanolamine, and less than 1% by weight of diethanolamine and monoethanolamine. By the expression "major part of triethanolamine" is here understood that said triethanolamine constitutes at least 50% by weight of the product mixture. The triethanol amine product mixture used in accordance with the invention can easily be obtained by reacting a conventional triethanolamine reaction mixture, obtained when reacting ammonia in one or more steps, with a $C_3$-$C_4$-alkylene oxide.

Such a process is described in British Patent No 1 140 867. Diethanolamine and monoethanolamine which are both reactants in the process have a catalytic effect and catalyze rather selectively their own alkoxylation. The presence of an effective amount of alkoxylation catalyst other than the diethanolamine and monoethanolamine shall preferably be avoided in order not to favour undesired side reactions. By the process, the contents of diethanolamine and monoethanolamine are reduced to less than 1% by weight, while the undesired side reactions, such as alkoxylation of hydroxyl groups or quarternization of the nitrogen atom, is kept on a low level. In order to further suppress side reactions, it has been found suitable to perform the reaction below 160° C., preferably between 120°-150° C. The amount of alkylene oxide added has to be adjusted in relation to the amount of diethanolamine and monoethanolamine, so that the latter ones can be alkoxylated to the corresponding tertiary amine. Normally, the molar ratio of the alkylene oxide to the reactive hydrogen atoms bound to the nitrogen in diethanolamine and monoethanolamine is 1.0-1.4 and suitably 1.0-1.10.

The choice of alkylene oxide affects the HLB-value of the triethanolamine mixture formed during the reaction and the butylene oxide may be preferred if a product mixture with the more hydrophobic and surface active character is desired. Normally, the alkylene oxide used is propylene oxide. Both propylene oxide and butylene oxides react with a high selectivity with respect to the hydrogen atoms bound to the nitrogen atom in the primary and secondary amine resulting in a lower degree of side reactions like propoxylation of hydroxyl groups in monoethanolamine, diethanolamine or triethanolamine.

The triethanol amine product mixture used in accordance with the invention has many advantageous properties. Thus, application tests have clearly indicated that the triethanolamine product mixture is very suitable to replace triethanolamine as a component in cosmetic formulations, such as shampoos and creams, and cleaning compositions, e.g., for hard surfaces. The diethanolmono-$C_3$-$C_4$-alkanolamine in the triethanolamine product mixture contributes to improved foaming properties.

DESCRIPTION OF THE PREFERRED EMBODIMENTS

The present invention is further illustrated by the following examples.

Example A 100 grams of a triethanolamine product mixture containing 85% by weight of triethanolamine and 15% by weight of diethanolamine and monoethanolamine (hereinafter referred to as TEA85) were reached with 8.4 grams of propylene oxide at 60° C. The ratio between the molecules of propylene oxide and the number of hydrogen atoms bound to a nitrogen atom was 1,01. After all propylene oxide had reacted the product obtained (hereinafter referred to as TEA85+PO) was analyzed with respect to the presence of secondary and primary ethanolamines. The total content of these alkanolamines was found to be less than 0.5% by weight.

Example B 100 grams of the same triethanolamine product mixture as specified in Example A were reacted with 10,4 grams of butylene oxide at 70° C. The ratio between the molecules of butylene oxide and the number of hydrogen atoms bound to a nitrogen atom was 1.00. After reaction with product mixture obtained (hereinafter referred to as TEA85-BO) was analyzed and the content of secondary and primary alkanolamines was found to be 0.7% by weight.

Example C 100 grams of the same triethanolamine products mixture as specified in Example A were reacted with 10.9 grams of propylene oxide at 150° C. The ratio between the molecules of propylene oxide and the number of hydrogen atoms bound to a nitrogen atom were 1.3. After reaction the content of secondary and primary alkanolamines was found to be less than 0.1% by weight.

Example 1

The triethanolamine product mixtures TEA85-PO and TEA85-BO from Examples A and B were diluted with water having a water hardness of 0.2° dH to solutions containing 3% by weight. The solutions were then neutralized with acetic acid to a pH-value of 9. As comparisons corresponding solution was also formulated from the triethanolamine product mixture used as starting product in Example A (hereinafter referred to as TEA85) and a distillation product of TEA85 containing 99% by weight of triethanolamine. The latter product are hereinafter referred to as TEA99.

The solutions of the alkanolamines were then tested with regard to foaming. 200 ml of each solution was vigorously stirred during 5 minutes and the volume of the fluid and the foam was measured. The following results were obtained.

| Alkanolamine | Volume[1] of foam and fluid ml Delay after stirring, min | | | |
|---|---|---|---|---|
| | 0 | 1 | 2 | 3 |
| TEA85 | 230 | 220 | 205 | 200 |
| TEA99 | 230 | 225 | 210 | 200 |
| TEA85-PO | 205 | 200 | | |
| TEA85-BO | 200 | | | |

[1]Volume of the solutions before stirring is 200 ml.

From the results it is evident that the product mixtures of the invention has a low foaming like the prior art products.

Example 2

Cleaning composition were formulated by mixing 5% by weight of $C_9H_{19}C_6H_4O(C_2H_4O)_4H$, 5% by weight of $C_9H_{19}C_6H_4O(C_2H_4O)_8H$, 40% by weight of any of the alkanolamines in the table below, 10% by weight of citric acid and 40% by weight of water (1.2° dH). The formulations were then diluted 20 times to ready-to-use solutions, which were tested at 20° C. with regard to their foaming ability in a standing cylinder rotating around a horizontal axis with a speed of 40 r.p.m.

| Alkanolamine | Upper level[1] of foam, mm Delay, sek | | |
|---|---|---|---|
| | 0 | 180 | 600 |
| TEA85 | 270 | 245 | 240 |
| TEA99 | 450 | 420 | 370 |
| TEA85-PO | 260 | 235 | 230 |
| TEA85-BO | 260 | 230 | 225 |

[1]The level of the washing solutions alone is 200 mm.

The washing solutions containing the alkanolamine products in accordance with the invention exhibit a very moderate foaming.

Example 3

Liquid soaps having the following compositions were prepared.

| Composition A | |
|---|---|
| Coco fatty acid salt of TEA85 | 17.1 |
| TEA85 | 1.8 |
| Antioxidant | 0.005 |
| Polyethylene glycol (MW 1500) | 0.95 |
| Glycerol | 1.1 |
| Hydroxyethyl cellulose | 1.0 |
| Na-tripolyphosphate | 1.0 |
| Water | balance |

| Composition B | |
|---|---|
| Coco fatty acid salt of TEA85-PO | 17.5 |
| TEA85-PO | 2.0 |
| Antioxidant | 0.005 |
| Polyethylene glycol (MW 1500) | 0.95 |
| Glycerol | 1.1 |
| Hydroxyethyl cellulose | 1.0 |
| Na-tripolyphosphate | 1.0 |
| Water | Balance |

The compositions were tested by a panel of six persons. No differences between the two compositions could be noticed by the panel, which indicates that the triethanolamine mixture of the invention with advantage could replace TEA85.

What is claimed is:

1. A method of providing a cosmetic product with defoaming properties, comprising:
    adding to the cosmetic product a triethanolamine product mixture which has not been distilled and which is comprised of:
    a major part by weight of triethanolamine;
    a minor part by weight of diethanolmono-$C_{3-4}$-alkanolamine and monoethanoldi-$C_{3-4}$-alkanolamine; and
    less than 1% by weight of a mixture of diethanolamine and monoethanolamine.

2. The method in accordance with claim 1, wherein the triethanolamine product mixture consists essentially of:
    a major part by weight of at least one triethanolamine;
    a minor part by weight of diethanolmono-$C_{3-4}$-alkanolamine and monoethanoldi-$C_{3-4}$-alkanolamine; and
    less than 1% by weight of a mixture of diethanolamine and monoethanolamine.

3. A method of providing a cleaning composition with defoaming properties, comprising:

adding to the cleaning composition a triethanolamine product mixture which has not been distilled and which is comprised of:
from 60–90% by weight of triethanolamine;
from 10–40% by weight of a mixture of diethanol-mono-$C_{3-4}$-alkanolamine and monoethanoldi-$C_{3-4}$-alkanolamine; and
less than 1% by weight of a mixture of diethanolamine and monoethanolamine.

4. The method in accordance with claim 3, wherein the triethanolamine product mixture consists essentially of:
from 60–90% by weight of triethanolamine;
from 10–40% by weight of a mixture of diethanol-mono-$C_{3-4}$-alkanolamine and monoethanoldi-$C_{3-4}$-alkanolamine; and
less than 1% by weight of a mixture of diethanolamine and monoethanolamine.

* * * * *